(12) United States Patent
Grass et al.

(10) Patent No.: US 6,654,444 B2
(45) Date of Patent: Nov. 25, 2003

(54) DIAGNOSTIC IMAGING METHOD

(75) Inventors: Michael Grass, Hamburg (DE); Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 154 days.

(21) Appl. No.: 10/056,086

(22) Filed: Jan. 24, 2002

(65) Prior Publication Data

US 2002/0114423 A1 Aug. 22, 2002

(30) Foreign Application Priority Data

Feb. 5, 2001 (DE) .......................... 012 00 393

(51) Int. Cl.⁷ ............................................. A61B 5/05
(52) U.S. Cl. ............................................. 378/20; 378/4
(58) Field of Search ................... 378/4, 20, 62, 378/68, 177

(56) References Cited

U.S. PATENT DOCUMENTS 5,186,174 A * 2/1993 Schlondorff et al. ........ 600/426
6,606,514 B2 * 8/2003 Grass et al. ................. 600/427
2001/0012327 A1 * 8/2001 Loser ........................... 378/42
2002/0128551 A1 * 9/2002 Grass et al. ................. 600/427
2003/0063292 A1 * 4/2003 Mostafavi ................... 356/614

FOREIGN PATENT DOCUMENTS

| EP | 0427358 A1 | 5/1991 | ............ A61B/6/00 |
|---|---|---|---|
| EP | 0930046 A2 | 7/1999 | ............ A61B/6/00 |
| WO | WO9625881 | 8/1996 | ............ A61B/8/08 |
| WO | WO0047103 | 8/2000 | |

* cited by examiner

*Primary Examiner*—Eric S. McCall
(74) *Attorney, Agent, or Firm*—Ernestine C. Bartlett

(57) ABSTRACT

The invention relates to a diagnostic imaging method for interventional radiology. According to this method layer images (1, 2) of the examination zone are reproduced in a three-dimensional view in such a manner that the trajectory of the interventional instrument (4) forms the common line of intersection (3) of the image planes of the layer images (1, 2). In accordance with the visualization method of the invention, at the same time a target zone (6, 6') that is to be reached by the interventional instrument (4) is displayed at the same time, so that the operating surgeon can interactively guide the interventional instrument (4) towards the target zone (6, 6').

10 Claims, 1 Drawing Sheet

DIAGNOSTIC IMAGING METHOD

Figure 1:
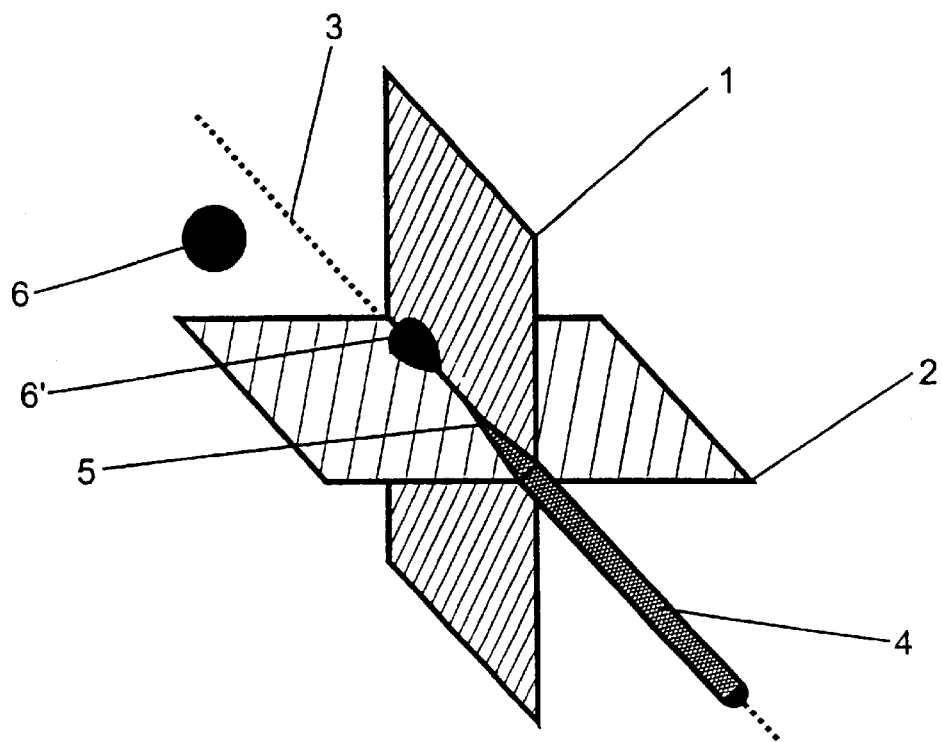

The invention relates to a diagnostic imaging method for the visualization of the position of an interventional instrument within an examination zone, in which method the position of the instrument is determined and reproduced in the form of an image simultaneously with at least two physiological layer images of the examination zone. The invention also relates to a CT apparatus for carrying out such a method and to a computer program for controlling a CT apparatus.

In interventional radiology a surgical intervention is performed while being monitored by way of a diagnostic imaging apparatus. The position of an interventional instrument, for example, a biopsy needle, a catheter or a probe within an examination zone is then determined. C-arm X-ray apparatus, CT tomography apparatus or also MR apparatus are customarily used for imaging. During the entire execution of the intervention image data is continuously acquired and visualized in such a manner that the surgeon can see the exact position of the instrument and guide it such that accidental damaging of internal organs is avoided and the target area of the intervention is reliably reached. The anatomical details in the vicinity of the interventional instrument are reproduced with a high spatial resolution during on-line monitoring of the examination zone by the imaging diagnostic apparatus, so that interventional radiology enables exact and effective interventions to be performed with only minimum physiological and psychological stress for the patient.

EP 0 860 144 A2 discloses a diagnostic imaging method in which imaging is performed by means of a CT apparatus in order to determine the position of an interventional instrument during a surgical intervention. A representation of the position of the interventional instrument is then superposed on the physiological volume image data of the examination zone. The combination of a reproduction of the instrument and the physiological image data yields a visualization of the position in the examination zone. To this end, the cited known method proposes to select layer images from the physiological volume image data that are also acquired by means of CT; two or more layer images are then displayed in such a manner that the operating surgeon can evaluate the position as well as the trajectory of the interventional instrument.

The cited known method has the drawback that, because of the limitation to two-dimensional layer images, the operating surgeon is offered no more than an inadequate spatial impression of the examination zone. Granted, the layer images reveal the anatomical details in the vicinity of the interventional instrument, but severe demands are made on the power of spatial imagination of the operating surgeon who must derive the spatial position of the instrument within the examination zone from the two-dimensional images in order to reach the target area of the intervention in a reliable manner and with the necessary foresight. According to the known method the interventional instrument can be guided in a controlled manner only when the exact trajectory of the instrument has already been defined in preparation of the intervention on the basis of pre-operative volume images of the examination zone.

Considering the foregoing, it is an object of the present invention to provide an improved visualization method for interventional radiology. The method should provide anatomically detailed reproduction of the local vicinity of the interventional instrument and should also simplify the guiding of the instrument by the surgeon by way of interactive imaging that provides a spatial impression of the position of the instrument in the examination zone.

This object is achieved by means of a diagnostic imaging method of the kind set forth that is characterized in accordance with the invention in that the image planes of the layer images are oriented parallel to the trajectory of the interventional instrument, the layer images being reproduced in a three-dimensional view of the examination zone in such a manner that the trajectory of the instrument constitutes the common line of intersection of the image planes.

The combination of a three-dimensional view of the examination zone with two-dimensional layer images from the vicinity of the interventional instrument in accordance with the invention enables local anatomical details to be reproduced simultaneously with a spatial view of the examination zone. Physiological structures are then displayed only within the image planes of the layer images and the remaining volume of the examination zone appears to be transparent. The layer images are reproduced in the three-dimensional view in such a manner that the position of the image planes in the examination zone is correctly shown. Because two or more layer images are simultaneously reproduced, a spatial impression of the anatomy in the examination zone is obtained. Because of the common line of intersection of the image planes, the trajectory of the instrument in the examination zone can be clearly distinguished; this fact substantially simplifies the interactive guiding of the instrument in comparison with the described previously known method. Moreover, it is thus ensured that the anatomy along the path of the interventional instrument is completely reproduced, so that unintentional injuries are avoided with certainty during the advancement of the instrument.

In conformity with the method in accordance with the invention, the physiological layer images can either be acquired and reconstructed continuously by means of an imaging diagnostic apparatus during the intervention or be generated from pre-operatively acquired volume image data. In that case, however, the pre-operative data set must be registered with the position of the patient during the intervention.

The method in accordance with the invention offers the possibility of display of curved trajectories of the interventional instrument in that the image planes of the layer images are also visualized with the corresponding curvature in the three-dimensional view of the examination zone.

In conformity with an advantageous further version of the method in accordance with the invention the relative spatial position of a target zone within the examination zone is reproduced in the three-dimensional view. A spatial survey image of the examination zone is thus produced, showing the instantaneous position of the interventional instrument as well as the target point of the intervention that is to be reached by the instrument. The surgeon is thus offered the opportunity to guide the instrument interactively on the basis of the images displayed, it being particularly simple to reach the desired target point by guiding the interventional instrument in such a manner that the target zone is situated on the common line of intersection of the image planes in the view in accordance with the invention. The target zone of the intervention is customarily localized and marked in pre-operative diagnostic image data. This fact can be readily utilized for the method in accordance with the invention by registering the spatial position of the marker with the image data acquired during the intervention.

The target zone can be visualized in an arbitrary manner in accordance with the invention; however, it is advantageous to form a three-dimensional physiological volume image of the target zone if, depending on the type of the intervention, the anatomical details in the direct vicinity of the target are of importance.

Furthermore, for the imaging method in accordance with the invention it is also advantageous to reproduce the position of the interventional instrument within the examination zone in the three-dimensional view, because the reproduction of the trajectory alone usually does not suffice to guide the instrument. To this end, either a three-dimensional volume image of the interventional instrument can be formed or the instantaneous position can be marked in a different manner.

In the visualization method in accordance with the invention the layer images can be reconstructed from volume image data of the examination zone. Such image data may be either pre-operatively acquired image data or image data that is acquired continuously during the intervention. Suitable volume image data is presented, for example, by CT apparatus or also by MR tomography apparatus. Alternatively, the layer images can also be reconstructed directly from fluoroscopic projection data as produced by X-ray diagnostic imaging methods.

The method in accordance with the invention offers special advantages in respect of imaging by means of three-dimensional computed tomography. The use of spiral CT apparatus with single-layer detection devices for the formation of volume image data has the insurmountable drawback of extremely low image rates, because image reconstruction can always take place only after a complete scan of the examination zone. Interactive image rates, as desirable for reliable guiding of an interventional instrument, cannot be realized in this manner. Granted, in cone beam CT a complete volume zone is scanned during each individual rotation of the radiation source and the detector. The reconstruction of a volume image data set from the projection data acquired by means of cone beam CT, however, is very intricate and demanding in respect of calculation time. Therefore, because of the low image rate, such imaging methods thus far are not very suitable for interventional applications.

In accordance with the method of the invention, the position and the orientation of the interventional instrument define the positions of the image planes for the layer images. Consequently, a set of points that are situated on these image planes is defined in the examination zone; the image reconstruction, for example, from projection data acquired by means of cone beam CT, can be limited to said set. Because of the reduced calculation effort, the method in accordance with the invention enables the reproduction of the layer images to be continuously updated in real time on the basis of the projection data instantaneously acquired by means of three-dimensional computed tomography; the operating surgeon is thus interactively offered instantaneous anatomical images from the vicinity of the interventional instrument. The possibility of dynamic updating of the image data reproduced in particular distinguishes the method in accordance with the invention from previously known methods in which pre-operative image data is used for visualization for the reasons described above. The main problem of such methods consists in the fact that changes of the anatomy that are due to patient motions can never be precluded. Therefore, the use of pre-operatively acquired volume images may even be risky, depending on the type of intervention carried out.

In the diagnostic imaging method in accordance with the invention it is advantageously possible to determine the position of the interventional instrument directly from the image data. To this end, either the reconstructed volume data or layer image data or the fluoroscopic projection data of the examination zone are used. Depending on the shape of the interventional instrument, projection images acquired in only a few fluoroscopy directions may advantageously suffice for accurate estimation of the position. The position is thus determined by analysis of the image data for which either the characteristic shape of the interventional instrument or the specific X-ray absorption properties are used. An external localization device can alternatively be used for the determination of the position of the instrument. Optical localization methods, where the interventional instrument is provided with, for example, light-emitting diodes whose position in space can be detected by means of suitable light sensors, are customarily used.

The method in accordance with the invention can be carried out by means of a CT apparatus that includes an X-ray source and a detection device that are rotatable about a patient table and also includes means for determining the position of an interventional instrument, the radiation source and the detector therein being controlled by a control unit and the detection unit communicating with a reconstruction unit that reconstructs image data of an examination zone from the detected X-ray signals so as to reproduce this data by means of a display unit, the reconstruction unit reconstructing from the X-ray signals layer images whose image planes are being oriented parallel to the trajectory of the interventional instrument, said layer images being reproduced by the display unit in a three-dimensional view of the examination zone in such a manner that the trajectory of the instrument constitutes the common line of intersection of the image planes.

It is advantageously possible to implement the method of the invention, without necessitating special adaptation of the hardware, in conventional diagnostic apparatus in clinical use, that is, merely by providing the reconstruction unit with suitable programming for the visualization in accordance with the invention.

A computer program that is suitable in this respect is a program that generates layer images from volume image data of an examination zone and from the position data of an interventional instrument, the image planes of said layer images being oriented parallel to the trajectory of the interventional instrument, and outputs the layer images to a display unit as a three-dimensional view of the examination zone in such a manner that the trajectory of the instrument constitutes the common line of intersection of the image planes. For the interactive imaging that takes place in real time during a surgical intervention that is monitored by way of computed tomography, it is advantageous to update the reproduction of the layer images continuously, the layer images being reconstructed from continuously acquired projection data and the image reconstruction being limited to the areas of the image planes of the layer images.

A computer program of this kind can be advantageously offered to the users of customary imaging diagnostic apparatus on suitable data carriers such as, for example, discs or CD-ROMs, but it can also be presented for downloading via a public data network (Internet).

Figure 2:
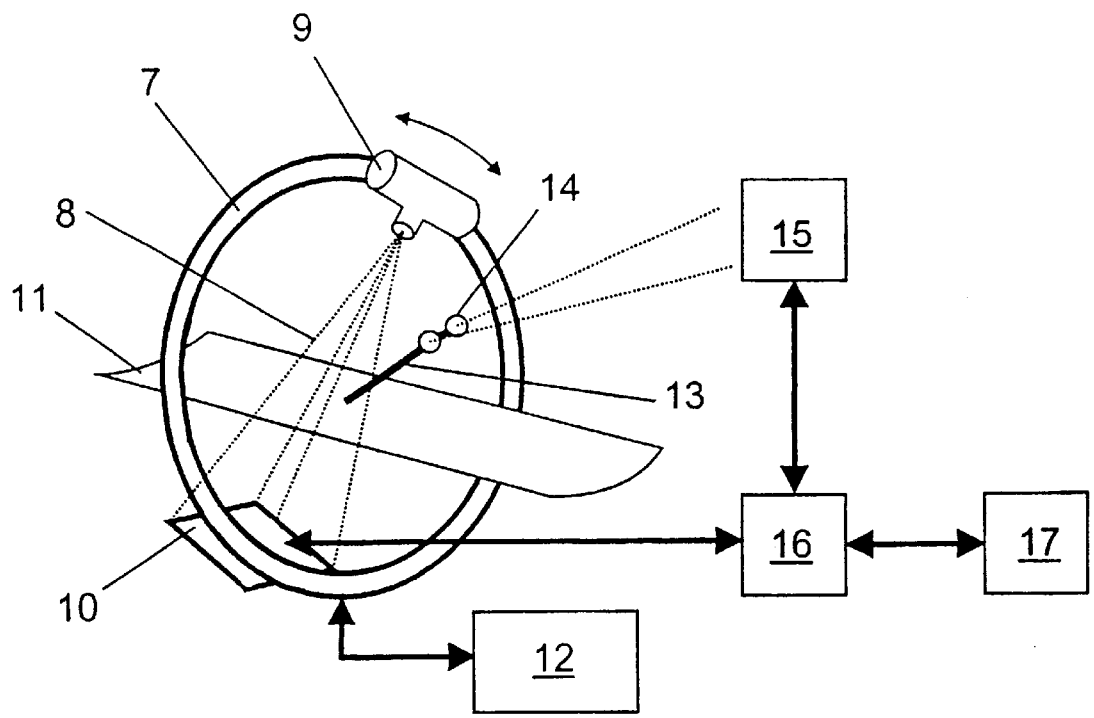

Embodiments of the invention will be described in detail hereinafter with reference to the Figures. Therein:

FIG. 1 is a three-dimensional view of the examination zone in accordance with the invention, FIG. 2 shows a CT apparatus in accordance with the invention.

FIG. 1 is a three-dimensional representation of a first layer image 1 and a second layer image 2. In this three-dimensional view the two layer images 1 and 2 are visualized in such a manner that the anatomical details to be recognized in the layer images are reproduced in the correct position in space because of the position of the image planes in space. The two layer images 1 and 2 are oriented so as to extend orthogonally to one another and intersect along a common line of intersection 3, the line of intersection 3 indicating the trajectory of an interventional instrument 4 in accordance with the invention. The interventional instrument 4 that is shown is a biopsy needle whose tip 5 is to be exactly localized within the examination zone in the three-dimensional view; the representation in perspective ensures that the position and the direction of the biopsy needle 4 can be recognized by the observer. By choosing a suitable viewing angle for the layer images 1 and 2, it is also achieved that the anatomical details in the vicinity of the needle tip 5 can be recognized exactly.

The three-dimensional view of the examination zone in FIG. 1 also shows a spherical marker 6 that characterizes a target zone that is to be reached by the tip 5 of the biopsy needle 4 during the intervention. The surgeon can clearly recognize that the sphere 6 is situated outside the line of intersection 3, it thus being indicated that the biopsy needle will miss the target zone 6 if it is displaced further along this trajectory. The target zone that is marked by the sphere 6' is situated clearly in the image planes of both layer images 1, 2 and on the line of intersection 3 and is hence reached by the biopsy needle 4.

The CT apparatus that is shown in FIG. 2 consists of a portal 7 on which an X-ray source 9 that emits a conical radiation beam 8 and an oppositely situated, flat radiation detector 10 rotate around a patient table 11. The X-ray source 9 and the detection device 10 are controlled by a control unit 12 that communicates with the portal 7. Above the patient table 11 there is situated, within the irradiated volume, a biopsy needle 13 that is provided with light-emitting diodes 14. The light that is emitted by the light-emitting diodes 14 is detected by means of an optical localization device 15 so that the position of the biopsy needle 13 in the examination zone is determined. The detection device 10 and the localization device 15 communicate with a reconstruction unit 16 that processes the position data of the biopsy needle 13 as well as the fluoroscopic projection data of the detection device 10 so as to select, in conformity with the invention, the image planes of the intersecting layer images and to output a three-dimensional view as described above for the display on a display unit 17.

What is claimed is:

1. A diagnostic imaging method for the visualization of the position of an interventional instrument (4) within an examination zone, in which method the position of the instrument (4) is determined and reproduced in the form of an image simultaneously with at least two physiological layer images (1, 2) of the examination zone, characterized in that the image planes of the layer images (1, 2) are oriented parallel to the trajectory (3) of the interventional instrument (4), the layer images (1, 2) being reproduced in a three-dimensional view of the examination zone in such a manner that the trajectory (3) of the instrument (4) constitutes the common line of intersection (3) of the image planes.

2. A method as claimed in claim 1, characterized in that the relative spatial position of a target zone (6) within the examination zone is reproduced in the three-dimensional view.

3. A method as claimed in claim 1, characterized in that the position of the interventional instrument within the examination zone is reproduced in the three-dimensional view.

4. A method as claimed in claim 1, characterized in that the layer images are reconstructed from fluoroscopic projection data, the image reconstruction being limited to the areas of the image planes of the layer images.

5. A method as claimed in claim 4, characterized in that the reproduction of the layer images is continuously updated on the basis of continuously acquired projection data.

6. A method as claimed in claim 1, characterized in that the position of the interventional instrument (4) is determined from volume image data or layer image data or from fluoroscopic projection data of the examination zone.

7. A method as claimed in claim 1, characterized in that the position of the interventional instrument (4) is determined by means of an external localization device (15).

8. A CT apparatus for carrying out the method claimed in claim 1, which apparatus includes an X-ray source (9) and a detection device (10) that are rotatable about a patient table (11), and also includes means (15) for determining the position of an interventional instrument (13), the radiation source (9) and the detector (10) being controlled by a control unit (12) and the detection device (10) communicating with a reconstruction unit (16) that reconstructs image data of an examination zone from the detected X-rays so as to reproduce this data by means of a display unit (17), characterized in that layer images whose image planes are oriented parallel to the trajectory of the interventional instrument (13) are reconstructed from the X-ray signals by means of the reconstruction unit (16), said layer images being reproduced by the display unit (17) in a three-dimensional view of the examination zone in such a manner that the trajectory of the instrument (13) constitutes the common line of intersection of the image planes.

9. A computer program for controlling an imaging diagnostic apparatus, notably a CT apparatus as claimed in claim 8, characterized in that it generates layer images from volume image data of an examination zone and from the position data of an interventional instrument, the image planes of said layer images being oriented parallel to the trajectory of the interventional instrument, and that it outputs the layer images to a display unit as a three-dimensional view of the examination zone in such a manner that the trajectory of the instrument constitutes the common line of intersection of the image planes.

10. A computer program as claimed in claim 9, characterized in that the reproduction of the layer images is continuously updated, the layer images being reconstructed from projection data continuously acquired by means of a CT apparatus, and the image reconstruction being limited to the areas of the image planes of the layer images.

* * * * *